(12) United States Patent
Ogihara et al.

(10) Patent No.: US 8,142,546 B2
(45) Date of Patent: *Mar. 27, 2012

(54) ARTIFICIAL LUNG

(75) Inventors: Mitsuaki Ogihara, Shizuoka (JP);
Hidetaka Nakayama, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/085,157

(22) Filed: Apr. 12, 2011

(65) Prior Publication Data

US 2011/0186514 A1 Aug. 4, 2011

Related U.S. Application Data

(63) Continuation of application No. 12/206,440, filed on Sep. 8, 2008, now Pat. No. 7,947,113, which is a continuation of application No. 11/179,743, filed on Jul. 13, 2005, now Pat. No. 7,431,754.

(30) Foreign Application Priority Data

Jul. 23, 2004 (JP) .................................. 2004-216448

(51) Int. Cl.
*B01D 53/22* (2006.01)
*B01D 61/00* (2006.01)
*B01D 19/00* (2006.01)
*A61M 1/16* (2006.01)

(52) U.S. Cl. ............... 95/45; 95/46; 95/51; 95/54; 96/8; 96/10; 210/650; 604/6.14; 422/45

(58) Field of Classification Search ............... 95/46, 45, 95/54, 241, 51; 96/6, 8, 10; 604/6.14, 6.15; 210/645, 650, 321.79; 422/45

See application file for complete search history.

(56) References Cited

U.S. PATENT DOCUMENTS

| | | | |
|---|---|---|---|
| 3,807,958 | A | 4/1974 | Brumfield et al. |
| 4,183,961 | A | 1/1980 | Curtis |
| 4,690,758 | A | 9/1987 | Leonard et al. |
| 5,034,188 | A | 7/1991 | Nakanishi et al. |
| RE33,932 | E | 5/1992 | Fukasawa et al. |
| 5,770,149 | A | 6/1998 | Raible |
| 6,503,451 | B2 | 1/2003 | Ikeda et al. |
| 6,723,283 | B2 | 4/2004 | Ghelli et al. |
| 6,730,267 | B2 | 5/2004 | Stringer et al. |

(Continued)

FOREIGN PATENT DOCUMENTS

EP 0049461 B1 4/1982

(Continued)

OTHER PUBLICATIONS

U.S. Appl. No. 11/655,126, filed Jan. 19, 2007, Ogihara et al.

(Continued)

*Primary Examiner* — Jason M Greene
(74) *Attorney, Agent, or Firm* — Buchanan Ingersoll & Rooney PC (57) ABSTRACT

An artificial lung includes a housing, a tubular hollow fiber membrane bundle contained in the housing and providing a multiplicity of hollow fiber membranes having a gas exchange function, a gas inflow port and a gas outflow port communicating with each other through hollow portions of the hollow fiber membranes, and a blood inflow port and a blood outflow port through which blood is distributed. The tubular hollow fiber membrane bundle has a cylindrical overall shape, and a filter member having a bubble-trapping function is provided on an outer peripheral portion of the tubular hollow fiber membrane bundle.

18 Claims, 6 Drawing Sheets

U.S. PATENT DOCUMENTS

| | | |
|---|---|---|
| 7,022,284 B2 | 4/2006 | Brian et al. |
| 2002/0049401 A1 | 4/2002 | Ghelli et al. |
| 2004/0054316 A1 | 3/2004 | Maianti et al. |

FOREIGN PATENT DOCUMENTS

| | | |
|---|---|---|
| EP | 0306613 B1 | 3/1989 |
| EP | 0 895 786 A1 | 2/1999 |
| EP | 1 108 462 A2 | 6/2001 |
| EP | 1 108 462 A3 | 7/2002 |
| EP | 1 180 374 B1 | 9/2004 |
| EP | 1618906 A1 | 1/2006 |
| JP | 63-267367 A | 4/1988 |
| JP | 2-213356 A | 8/1990 |
| JP | 7-328114 A | 12/1995 |
| JP | 8-19601 A | 1/1996 |
| JP | 11-137671 A | 5/1999 |
| WO | WO 97/16213 A2 | 5/1997 |
| WO | WO 00/06357 A1 | 2/2000 |

OTHER PUBLICATIONS

U.S. Appl. No. 11/654,599, filed Jan. 18, 2007, Ogihara.
U.S. Appl. No. 11/727,608, filed Mar. 27, 2007, Mizoguchi et al.

ARTIFICIAL LUNG

This application is a continuation of application Ser. No. 12/206,440 filed on Sep. 8, 2008, which is a continuation of application Ser. No. 11/179,743 filed on Jul. 13, 2005. This application is also based on and claims priority under 35 U.S.C. §119 with respect to Japanese Application No. 2004-216448 filed on Jul. 23, 2004, the entire content of which is incorporated herein by reference.

FIELD OF THE INVENTION

The present invention generally relates to an artificial lung.

BACKGROUND DISCUSSION

Conventional artificial lungs include those having a hollow fiber membrane bundle. An example of such an artificial lung is described in Japanese Patent Laid-Open No. Hei 11-47268, corresponding to European Application Publication No. 0 895 786.

This artificial lung includes a housing, a hollow fiber membrane bundle (hollow fiber membrane accumulation) contained in the housing, a blood inflow port and a blood outflow port, and a gas inflow port and a gas outflow port. In the event bubbles are present in the blood flowing in via the blood inflow port of the artificial lung having such a configuration, it is preferable that the bubbles are removed by the hollow fiber membrane bundle.

However, problems arise in that the bubbles are not sufficiently removed by the hollow fiber membrane bundle and might flow out to the blood outflow port together with the blood.

SUMMARY

According to one aspect of the present invention, an artificial lung includes: a housing; a hollow fiber membrane bundle contained in the housing and in which a multiplicity of hollow fiber membranes having a gas exchanging function are accumulated; a gas inflow portion and a gas outflow portion communicated with each other through the lumens of the hollow fiber membranes; and a blood inflow portion and a blood outflow portion in which blood flows. The hollow fiber membrane bundle has a cylindrical overall shape. A bubble trapping filter member which is adapted to trap bubbles is provided at an outer peripheral portion of the hollow fiber membrane bundle or at an intermediate portion in the thickness direction of the hollow fiber membrane bundle.

Preferably, the filter member is provided in contact with an outer peripheral portion of the hollow fiber membrane bundle and covers substantially the entire part of the outer peripheral portion. In the artificial lung, a gap is preferably formed between the filter member and the housing.

Preferably, the blood inflow portion has an inflow opening portion opening to the inner peripheral portion side of the hollow fiber membrane bundle, while the blood outflow portion has an outflow opening portion opening to the outer peripheral portion side of the hollow fiber membrane bundle, and the blood passes from the inner peripheral portion side to the outer peripheral portion side of the hollow fiber membrane bundle.

The filter member may be hydrophilic. In addition, the filter member may be mesh-like. The opening of the filter member is preferably not more than 50 μm.

According to another aspect, an artificial lung comprises a housing comprising a blood inflow port through which blood flows, a blood outflow port through which blood flows, a gas inflow port through which flows gas and a gas outflow through which flows gas. A tubular hollow fiber membrane bundle is positioned in the housing and comprises a plurality of hollow fiber membranes, with the gas inflow port communicating with the hollow fiber membrane bundle and the gas outflow port communicating with the hollow fiber membrane bundle. A first annular blood chamber is positioned radially inwardly of the hollow fiber membrane bundle and communicates with the blood inflow port, and a second annular blood chamber is positioned radially outwardly of the hollow fiber membrane bundle and communicates with the blood outflow port. An annular bubble trapping filter member is positioned in the housing between a circumferential inner surface of the housing and the first annular blood chamber to trap bubbles contained in blood in the hollow fiber membrane bundle.

The embodiments of the artificial lung described here are able to relatively securely trap bubbles present in the blood by the filter member provided at the hollow fiber membrane bundle. It is thus possible with the artificial lung described here to relatively reliably prevent the bubbles from flowing out from the blood outflow portion.

BRIEF DESCRIPTION OF THE DRAWING FIGURES

The above and other features and characteristics of the artificial lung will become more apparent from the following detailed description considered together with the accompanying drawing figures in which like elements are designated by like reference numerals.

DETAILED DESCRIPTION

Referring generally to FIGS. 1-5, one embodiment of the artificial lung 1 includes a tubular core 5, a tubular (cylindrical) hollow fiber membrane bundle 3 in which are accumulated a multiplicity of gas exchange hollow fiber membranes 3a, which are adapted to perform a gas exchange function, wound around the outer surface of the tubular core 5, a housing for containing the tubular hollow fiber membrane bundle 3 therein, a gas inflow portion and a gas outflow portion communicating with each other through the inside (lumen) of the hollow fiber membranes 3a, a blood inflow portion and a blood outflow portion for communication between the exterior of the hollow fiber membranes 3 and the inside of the housing, and a filter member 6 provided at the tubular hollow fiber membrane bundle 3. The tubular hollow fiber membrane bundle 3 has a structure in which hollow fiber membrane layers (hollow fiber membranes 3a) spread on the outer peripheral surface of the tubular core 5 are stacked in a multi-layer form, i.e., stacked or layered in a spiral form, or taken up into a reel form, with the tubular core as a core. Further, the hollow fiber membrane layers are so configured that an intersection portion 3b where the hollow fiber membranes 3a intersect each other is provided in the vicinity of the center in the longitudinal direction of the tubular core 5, with the intersection portions 3b being located at different positions so that one intersection portion 3b is not stacked directly on another intersection portion 3b, or a direct stacking of one intersection portion 3b and another intersection portion 3b does not occur.

The artificial lung 1 includes the housing 2, an artificial lung unit contained in the housing 2, and a tubular heat exchanger unit contained in the artificial lung unit so that the artificial lung is a heat exchange function-incorporating artificial lung.

The artificial lung 1 comprises: the artificial lung unit which includes the tubular core 5, the tubular hollow fiber membrane bundle 3 having a multiplicity of gas exchange hollow fiber membranes wound around the outside surface of the tubular core 5, and a filter member 6; the tubular heat exchanger unit contained in the tubular core 5; and the housing 2 containing the artificial lung unit and the tubular heat exchanger unit therein. The outwardly facing surface of the tubular core 5 is provided with a plurality of grooves 51 forming blood conduits between the outside surface of the tubular core 5 and the inside surface of the tubular hollow fiber membrane bundle 3. The tubular core 5 is also provided with a blood flow opening(s) 52 providing communication between a first blood chamber 11, formed between the tubular core 5 and the tubular heat exchanger unit, and the grooves 51.

The artificial lung 1 has a blood inflow port (blood inflow portion) 24 communicating with the first blood chamber 11 (the inner peripheral portion side of the tubular hollow fiber membrane bundle 3) formed between the tubular core 5 and the tubular heat exchanger unit, and a blood outflow port (blood outflow portion) 25 communicating with a second blood chamber 12 (the outer peripheral portion side of the tubular hollow fiber membrane bundle 3) formed between the outside surface of the tubular hollow fiber membranes and the inside surface of the housing 2.

In addition, the blood inflow port 24 is provided with an inflow opening portion 40 opening into the first blood chamber 11. This helps ensure that blood from the blood inflow port 24 flows assuredly into the first blood chamber 11. The blood in the first blood chamber 11 passes through a blood distribution opening(s) 52 and through an inner peripheral portion 15 of the tubular hollow fiber membrane bundle 3 into the inside 16 of the tubular hollow fiber membrane bundle 3. In addition, the blood which has flowed into the inside 16 of the tubular hollow fiber membrane bundle 3 flows via an outer peripheral portion 17 of the tubular hollow fiber membrane bundle 3 into the second blood chamber 12.

In addition, the blood outflow port 25 is provided with an outflow opening portion 43 opening into the second blood chamber 12. This helps ensure that the blood in the second blood chamber 12 flows out to the blood outflow port 25 assuredly.

Figure 3:
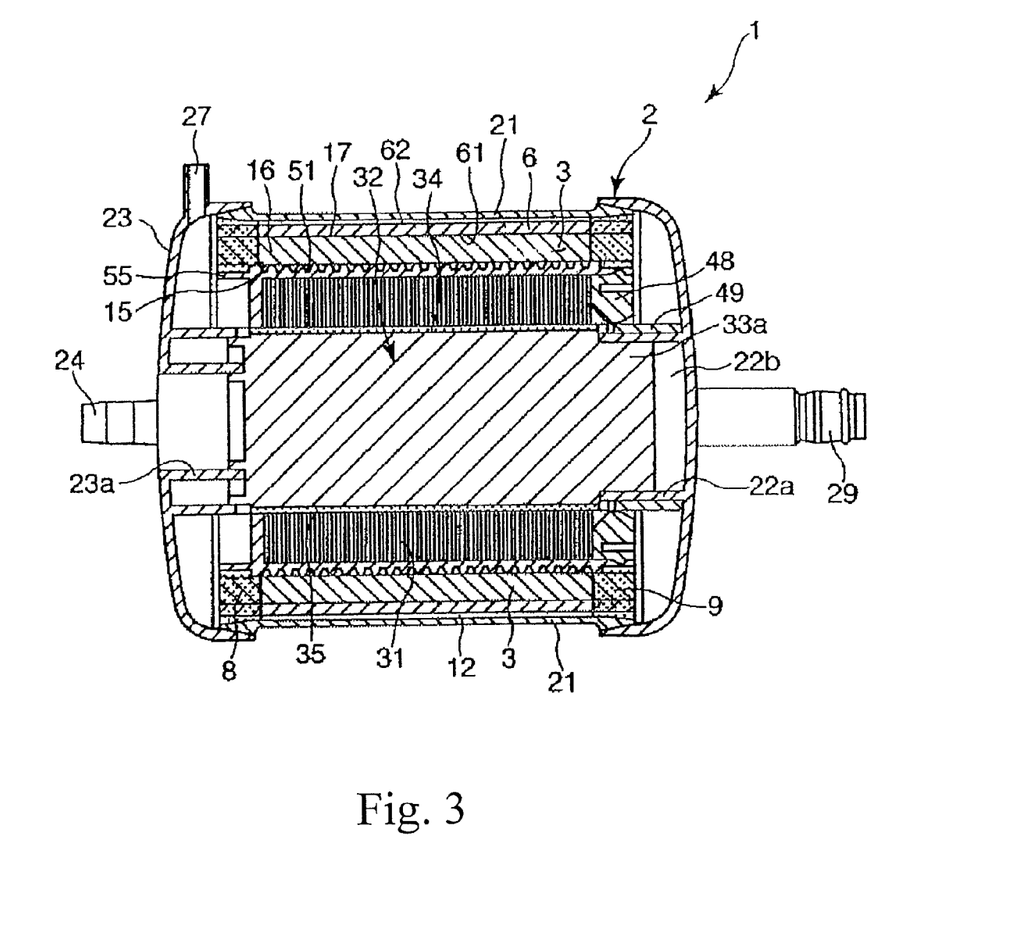
FIG. 3 is a cross-sectional view along line A-A of FIG. 2.
Figure 4:
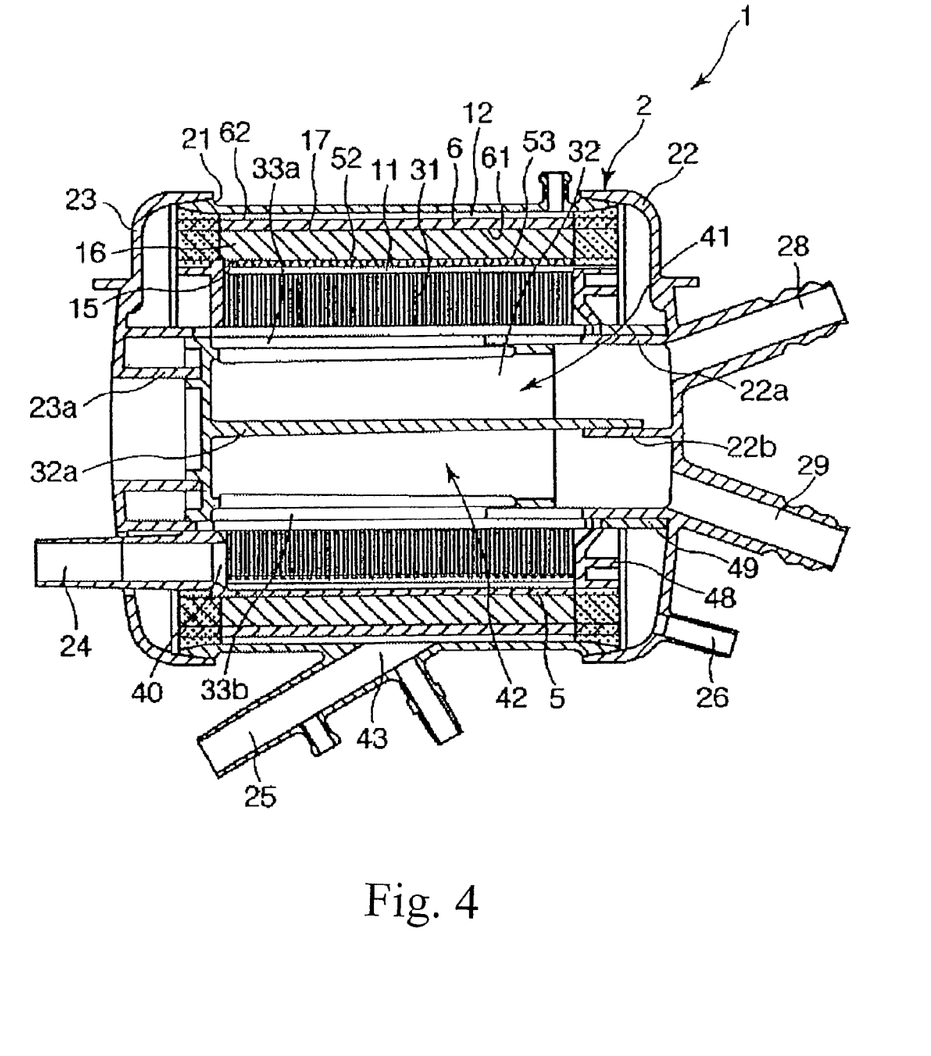
FIG. 4 is a cross-sectional view along line B-B of FIG. 2.
Figure 5:
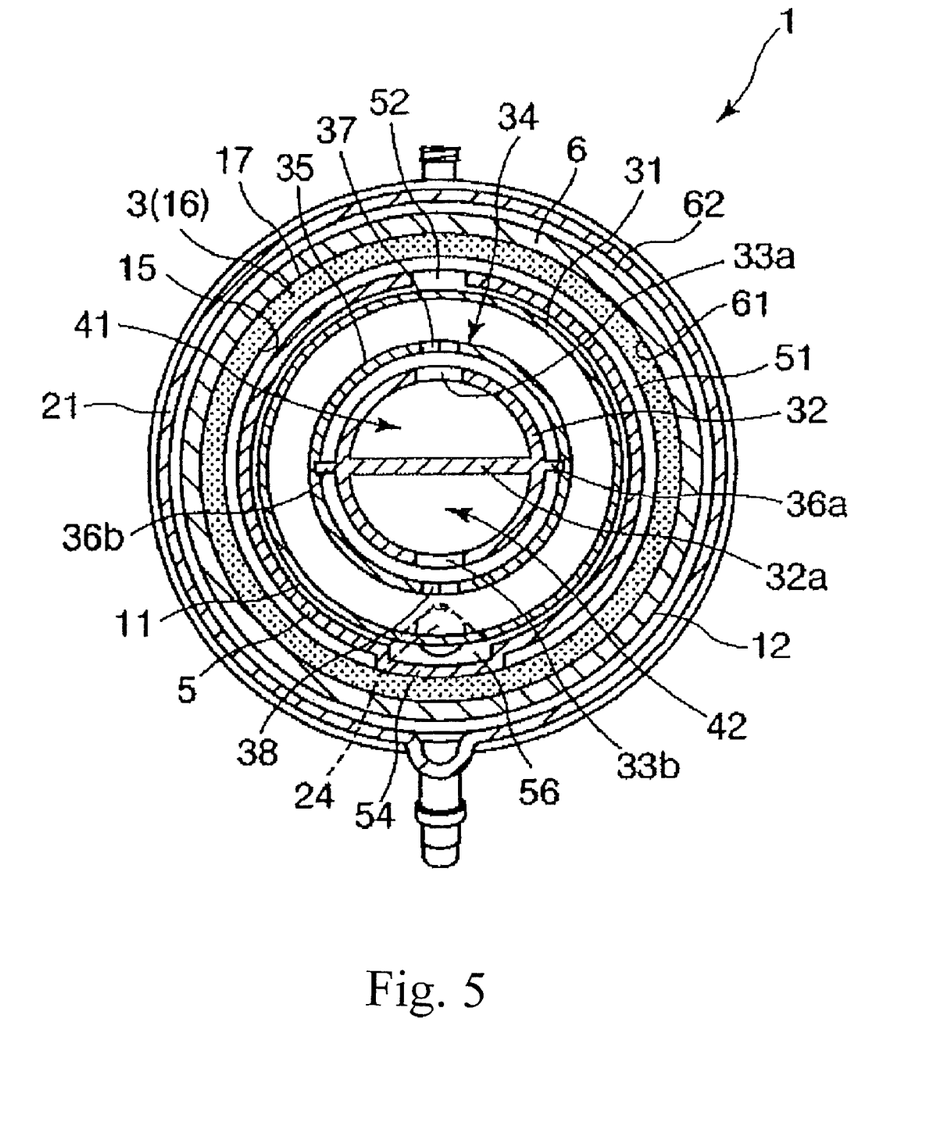
FIG. 5 is a cross-sectional view along line C-C of FIG. 1.

As shown in FIGS. 3 to 5, in the artificial lung 1, a tubular housing body 21, the second blood chamber 12, the hollow fiber membrane bundle 3, the tubular core 5 having the grooves 51, the first blood chamber 11, a tubular heat exchanger 31, tubular heat exchanger deformation restraining portions 34, 35, and a tubular heating medium forming member 32 are arranged or formed concentrically in this order from the outside. As shown in FIG. 1 and FIGS. 3 to 5, the housing 2 includes the tubular housing body 21 having the blood outflow port 25; a first header 22 having a gas inflow port (gas inflow portion) 26, a heating medium inflow port 28 and a heating medium outflow port 29; and a second header 23 having a gas outflow port (gas outflow portion) 27 and an insertion port for the blood inflow port 24 provided in the tubular core 5. The first header 22 is provided at its inside surface with a heating medium chamber forming member connection portion 22a projecting in a tubular form, and a partition portion 22b bisecting or dividing the inside of the heating medium chamber forming member connection portion 22a. In addition, the second header 23 is provided at its inside surface with a heating medium chamber forming member connection portion 32 projecting in a tubular form. As shown in FIG. 4, a tubular heating medium chamber forming member 32 described later has an opening end side held by the first header 22 and a closed end side held by the second header 23.

The artificial lung unit includes the tubular core 5, the tubular hollow fiber membrane bundle 3 having a multiplicity of hollow fiber membranes wound around the outside surface of the tubular core 5, and the filter member 6 provided on the outer peripheral portion 17 of the tubular hollow fiber membrane bundle 3.

As shown in FIGS. 3 to 5, the tubular core 5 is tubular in shape. An annular plate-like projecting portion 55 extending on the inside with a predetermined width is formed at one end of the tubular core 5, and the blood inflow port 24 is formed at the outside surface of a flat surface portion of the annular plate-like projecting portion 55 in parallel to the center axis of the tubular core 5 so as to project outwards. The outside surface of the tubular core 5 is provided with the multiplicity of grooves 51 forming blood conduits between the outside surface of the tubular core 5 and the inside surface of the tubular hollow fiber membrane bundle 3.

The tubular core 5 also has the blood distribution opening(s) 52 providing communication between the grooves 51 and the first blood chamber 11 which is formed between the tubular core 5 and the tubular heat exchanger unit. The tubular core 5 possesses an outside diameter that is preferably about 20 to 100 mm, and an effective length (i.e., the length of the portion not buried in the partition wall) of preferably about 10 to 730 mm. More specifically, the plurality of grooves 51 of the tubular core 5 are parallel to one another, but not continuous, and axially spaced apart over a range of the core exclusive of both end portions. In addition, the portions between the axially adjacent grooves 51 are provided as annular ribs 53.

The grooves in the tubular core 5 are so formed as to be present over substantially the whole area of that portion of the hollow fiber membrane bundle which contributes to gas exchange (the effective length, or the portion not buried in the partition wall). As generally shown in FIG. 5, the tubular core 5 used here has a non-grooved portion 54 (of a generally flat surface form) which is located substantially on an extension line of the blood inflow port 24 and extends substantially over the entirety of the grooved portion of the tubular core 5. Therefore, the grooves 51 and the ribs 53 of the tubular core 5 are formed as annular grooves 51 (arcuate grooves and annular ribs 53 (arcuate ribs) having starting ends and finishing ends (i.e., the grooves and ribs are not continuous). As mentioned, the non-grooved portion 54 of the core 5 extends substantially over the whole part (i.e., axial extent) of the grooved portion of the tubular core 5, whereby shape stability of the tubular hollow fiber membrane bundle 3 provided at the outside surface of the tubular core 5 is enhanced.

However, it is to be understood that the non-grooved portion 54 is not indispensable, as the grooves 51 and the ribs 53 of the tubular core 5 may be endless fully annular grooves 51 and endless fully annular ribs 53, respectively.

The tubular core 5 is provided with the grooves 51 over substantially the entire range of the effective length (the portion not buried in the partition wall) of the hollow fiber membrane bundle 3 so that it is possible to disperse the blood to substantially the whole part of the hollow fiber membrane bundle 3, thus effectively utilizing substantially the whole part of the hollow fiber membranes and achieving a relatively high gas exchange performance.

Further, the top of each of the ribs 53 formed between the grooves 51 of the tubular core 5 is preferably a generally flat surface, meaning that the top of each of the ribs is not pointed. With the ribs 53 thus formed as generally flat surfaces, shape stability of the tubular hollow fiber membrane bundle 3 formed on the outside surface of the tubular core 5 is enhanced.

As generally seen in FIG. 3, the cross-sectional shape of each of the ribs 53 is a shape that narrows toward the top of the rib (i.e., in a direction toward the hollow fiber membrane bundle 3. The ribs may thus possess a somewhat trapezoidal shape in cross-section). This helps ensure that the grooves 51 (blood conduits) are each broadened toward the inside surface of the hollow fiber membrane bundle so that the blood flows into the hollow fiber membrane bundle favorably.

In addition, the blood inflow port 24 is provided on the side of one end portion of the tubular core 5, and the blood distribution opening(s) 52 is formed in a region opposed to a region obtained by extending the center line of the blood inflow port 24. This helps provide a relatively uniform blood distribution in the first blood chamber 11 formed between the tubular core 5 and the tubular heat exchanger unit, and can also enhance the heat exchange efficiency.

More specifically, as shown in FIG. 5, the non-grooved portion 54 is circumferentially located substantially on the extension line of the blood inflow port 24 (i.e., the axis or center line of the blood inflow port 24 circumferentially coincides with the location of the non-grooved portions 54) and extends over substantially the entire axial extent of the grooved portion. The non-grooved portion 54 is a thinner portion (i.e., thinner in the radial direction) enabled by the absence of the grooves, whereby a blood guide portion 56 circumferentially located substantially on the extension line of the blood inflow port 24 (on the axial extension of the center line of the blood inflow port 24) is formed in the inside of the tubular core 5. The blood guide portion 56 is larger in inside diameter than the grooved portions. With the blood guide portion 56 thus provided, it is possible to cause the blood to relatively reliably flow into the whole part in the axial direction of the first blood chamber 11 formed between the tubular core and the tubular heat exchanger unit.

In this disclosed embodiment of the artificial lung, a plurality of blood distribution openings 52 are provided in the tubular core 5 and are individually communicated with the plurality of annular grooves 51. The blood distribution openings 52 are circumferentially located in a region or location that is opposed (diametrically opposed) to the non-grooved portion 54 (blood guide portion 56). One of the ribs 53 is present between the adjacent openings 52.

Figure 1:
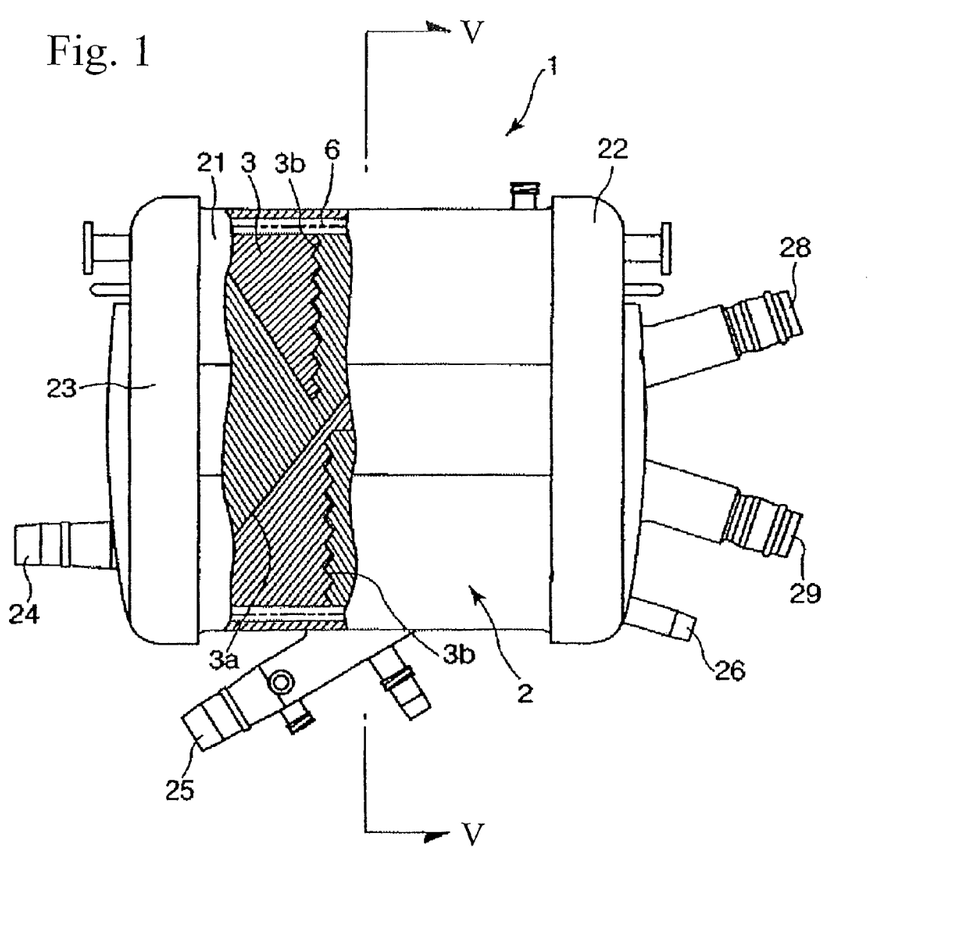
FIG. 1 is a front view of an artificial lung according to a first embodiment of the present invention.
Figure 2:
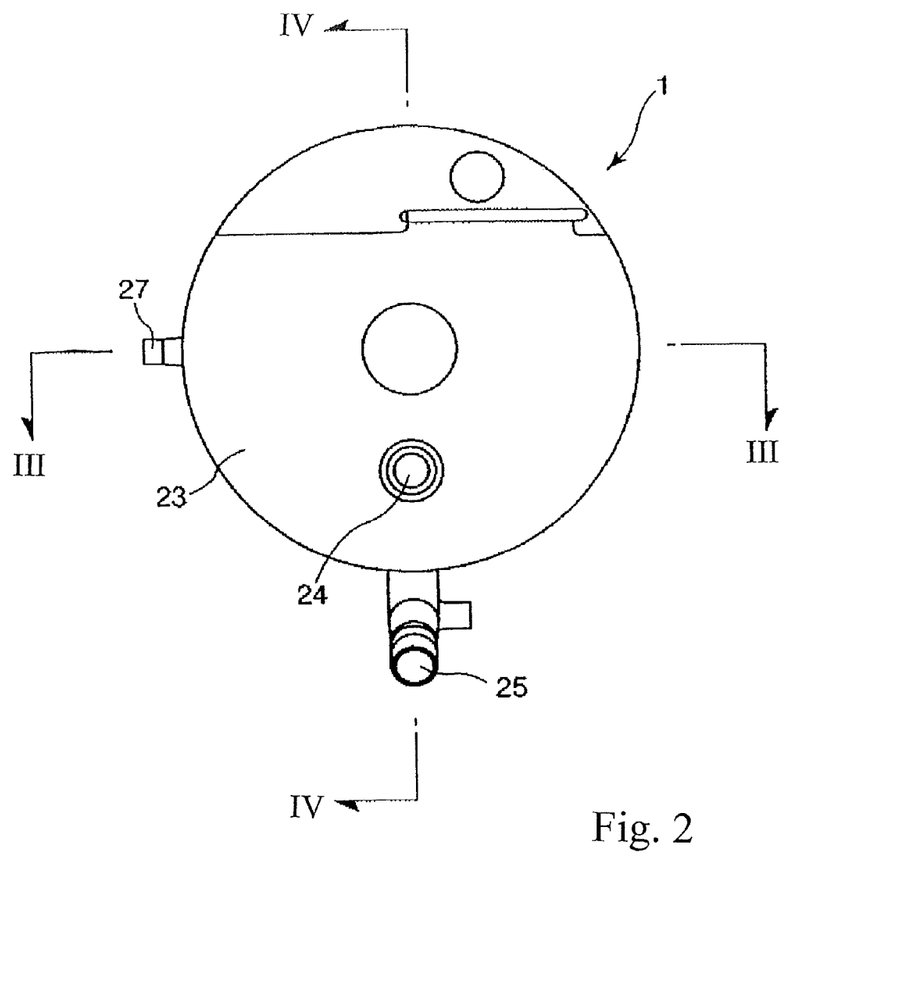
FIG. 2 is a left side view of the artificial lung shown in FIG. 1.

As shown in FIG. 4, the hollow fiber membrane bundle 3 is wound around the outside surface of the tubular core 5. The hollow fiber membranes 3a forming the hollow fiber membrane bundle 3 are sequentially wound around the tubular core 5, as shown in FIG. 1, whereby the hollow fiber membrane layers spread on the outer peripheral surface of the tubular core 5 are stacked in a multi-layer form, i.e., stacked in a spiral form or taken up into a reel form with the tubular core 5 as a core.

The hollow fiber membrane bundle 3 is formed by winding the hollow fiber membranes around the tubular core 5, fixing both ends of the hollow fiber membranes to the tubular housing body 21 by partition walls 8, 9, and cutting both ends of the hollow fiber membrane bundle 3. Both ends of the tubular core 5 with the hollow fiber membrane bundle 3 wound around the outside surface thereof are fixed in a liquid-tight manner to both end portions of the tubular housing body 21 by the partition walls 8, 9, and the second blood chamber 12 as an annular space (tubular space) is located between the outside surface of the tubular hollow fiber membranes and the inside surface of the tubular housing body 21.

The blood outflow port 25 formed at a side surface of the tubular housing body 21 communicates with the second blood chamber 12. The partition walls 8, 9 are each preferably formed of a potting agent such as polyurethane and silicone rubber.

In addition, the hollow fiber membrane bundle has intersection portions 3b where the hollow fiber membranes 3a intersect in the vicinity of the center in the longitudinal direction of the tubular core 5. The intersection portions (cross wind portions) 3b are located differently depending on the portion of the hollow fiber membrane bundle. With the position of the intersection portions thus varied, the intersection portions in the overlapping layers do not overlap one another as shown in FIG. 1, whereby short-circuiting of the blood due to the overlapping of the intersection portions can be inhibited or prevented from occurring. The intersection portions are formed continuously by, for example, a configuration in which two to six hollow fiber membranes wound substantially in parallel intersect alternately.

As the hollow fiber membranes, a porous gas exchange member is used. As the porous hollow fiver membrane, there can be used one which has an inside diameter of 100 to 1000 µm, a material thickness of 5 to 200 µm, preferably 10 to 100 µm, a porosity of 20% to 80%, preferably 30% to 60%, and a pore diameter of 0.01 to 5 µm, preferably 0.01 to 1 µm.

As the material used for the porous film, a hydrophobic polymeric material such as polypropylene, polyethylene, polysulfone, polyacrynonitrile, polytetrafluoroethylene, cellulose acetate, etc. is used. Among these materials, polyolefin resin is a preferred material, and polypropylene is particularly preferred. It is more preferable to use a material whose wall is provided with micro-pores by an orientation method or a solid-liquid phase separation method.

The outside diameter (overall size) of the hollow fiber membrane bundle 3 is preferably 30 to 162 mm, and the thickness of the hollow fiber membrane bundle 3 is preferably 3 to 28 mm.

As shown in FIGS. 3-5, a filter member 6 is provided on the outer peripheral portion 17 of the tubular hollow fiber membrane bundle 3. The filter member 6 has the function of trapping bubbles present in the blood flowing into the artificial lung 1 (tubular hollow fiber membrane bundle 3).

In addition, like the tubular hollow fiber membrane bundle 3, the filter member 6 is cylindrical in overall shape. With the filter member 6 having such a shape, the inner peripheral portion (inner peripheral surface) 61 if the filter member 6 is in contact with the outer peripheral portion (outer peripheral surface) 17 of the tubular hollow fiber membrane bundle 3. In addition, the filter member 6 is provided so as to cover substantially the whole part of the outer peripheral portion 17 of the tubular hollow fiber membrane bundle 3.

With the filter member 6 thus provided, it is possible to enlarge the area of the filter member 6 (inner peripheral portion 61) and, therefore, to trap the bubbles more assuredly. In addition, the large area of the filter member 6 makes it possible to restrain or prevent the blood flow from being blocked, even upon generation of clogging (for example, with a coagulated lump of blood) at a part of the filter member 6.

As shown in FIG. 3, the second blood chamber 12 in the form of an annular gap is located between the filter member 6 and the housing 2. This makes it possible to prevent the filter member 6 from making contact with the inner peripheral surface of the housing 2, and to enable the blood flowing out from the outer peripheral portion 62 of the filter member 6 to pass through the inside of the second blood chamber 12 and, therefore, reach (flow into) the blood outflow port 25 relatively assuredly.

In addition, the filter member 6 is preferably hydrophilic. Specifically, it is preferable that the filter member 6 itself is formed of a hydrophilic material or the surface of the filter member 6 is subjected to a hydrophilicity-imparting treatment (for example, plasma treatment or the like). This helps ensure that the removal of bubbles at the time of priming is easy to carry out, whereby it is more difficult for the bubbles to pass when the blood with the bubbles mixed therein passes, and outflow of the bubbles from the filter member 6 can be restrained effectively.

The material constituting the filter member 6 is not particularly limited. By way of example, a mesh-like material (screen filter) is preferable as the constituent material. This makes it possible to trap the bubbles more assuredly and to allow the blood to pass through the filter member 6 relatively easily.

The size of the openings of the filter member 6 are not particularly limited, although the openings are preferably not more than 50 μm, more preferably in the range of 20 to 45 μm. This helps promote a relatively reliable trapping of the bubbles.

The filter member 6 configured as above contributes to achieving relatively reliable trapping of the bubbles present in the blood flowing from the first blood chamber 11 into the tubular hollow fiber membrane bundle 3, so that the bubbles can be relatively securely prevented from flowing out via the blood outflow port 25.

In addition, the bubbles trapped by the filter member 6 enter (flow) into the multiplicity of pores formed in the hollow fiber membranes 3a (tubular hollow fiber membrane bundle 3) as the pressure at the blood side is higher than inside the lumens of the hollow fiber membrane bundle. The bubbles are thus discharged (flow out) from the gas outflow port 27 after passing through the lumens of the hollow fiber membranes 3a. As a result, the time taken for priming the bubbles can be shortened, and the bubbles can be prevented from stagnating in the tubular hollow fiber membrane bundle 3 (artificial lung 1). The filter member 6 need not necessarily be so provided as to cover substantially the whole part of the outer peripheral portion 17 of the tubular hollow fiber membrane bundle 3. For example, the filter member 6 may be so provided as to cover a part of the outer peripheral portion 17 of the tubular hollow fiber membrane bundle 3.

As shown in FIGS. 3-5, a heat exchanger unit is contained in the inside of the tubular core 5 of the artificial lung unit formed as mentioned above. Various features pertaining to the heat exchanger unit will now be described.

The annular first blood chamber 11 is formed between the tubular core 5 and the tubular heat exchanger unit, and the blood inflow port 24 communicates with this blood chamber 11. As shown in FIGS. 3-5, the tubular heat exchanger unit includes a tubular heat exchange body 31, a tubular heating medium chamber forming member 32 contained in the heat exchange body 31, and two tubular heat exchange body deformation restraining portions 34, 35 inserted between the tubular heat exchange body 31 and the tubular heating medium chamber forming member 32.

As the tubular heat exchange body 31, a so-called bellows type heat exchange body is used. As shown in FIG. 4, the bellows type heat exchange body 31 (bellows pipe) includes a bellows forming portion having a multiplicity of hollow annular projections formed substantially parallel to a central side surface thereof, and cylindrical portions formed at both ends of the bellows forming portion and having an inside diameter approximately equal to that of the bellows forming portion. One of the cylindrical portions of the heat exchange body 31 is clamped between the inside surface of a side end portion of the blood inflow port 24 of the hollow tubular core 5 and a second header 23, and the other of the cylindrical portions of the heat exchange body 31 is clamped between the first header 22 and a tubular heat exchange body fixing member 49, which is inserted between a ring-like heat exchange body fixing member 48 inserted in one end of the hollow tubular core 5 and the first header 22.

The bellows type heat exchange body 31 is formed in a so-called minute bellows-like form, from a metal such as stainless steel, aluminum, etc. or a resin material such as polyethylene, polycarbonate, etc. A metal such as stainless steel and aluminum is preferably used, from the viewpoint of strength and heat exchange efficiency. Particularly, the bellows type heat exchange body 31 is composed of a bellows pipe assuming a wavy shape obtained by repetition of a multiplicity of recesses and projections substantially orthogonal to the axial direction (center axis) of the tubular heat exchange body 31.

As shown in FIGS. 3-5, the tubular heating medium chamber forming member 32 is a tubular body opened at one end (on the side of the first header 22), and includes a partition wall 32a for partitioning the inside into an inflow side heating medium chamber 41 and an outflow side heating medium chamber 42, a first opening 33a communicated with the inflow side heating medium chamber 41 and extending in the axial direction, a second opening 33b communicated with the outflow side heat exchange chamber 42 and extending in the axial direction, and projections 36a and 36b. These projections 36a, 36b are diametrically opposed to each other, are formed on the side surfaces at positions deviated by about 90° from the first opening 33a and the second opening 33b, project radially outwardly, and extend in the axial direction. The projection 36a enters into a groove formed at the center of the inside surface of the heat exchange body deformation restraining portion 34 and extends in the axial direction to thereby restrain the heat exchange body deformation restraining portion 34 from being moved. Similarly, the projection 36b enters into a groove formed at the center of the inside surface of the heat exchange body deformation restraining portion 35 and extends in the axial direction, to thereby restrain the heat exchange body deformation restraining portion 35 from being moved.

When the opening end side of the tubular heating medium chamber forming member 32 is fitted in a heating medium chamber forming member connection portion 22a of the first header 22 as shown in FIG. 4, a partition portion 22b for bisecting the inside of the tubular connection portion 22a makes close contact with one surface (in this embodiment, the lower surface) of a tip end portion of the partition wall 32a of the tubular heating medium chamber forming member 32. As a result the inflow side heating medium chamber 41 in the tubular heating medium chamber forming member 32 is communicated with the heating medium inflow port 28, and the outflow side heating medium chamber 42 is communicated with the heating medium outflow port 29.

In addition, the two heat exchange body deformation restraining portions 34, 35 are provided at their abutting end portions with cutout portions extending in the axial direction. When the two restraining portions 34, 35 are assembled to abut against each other as shown in FIG. 5, a medium inflow side passage 37 and a medium outflow side passage 38 are formed. It is to be understood that the two heat exchange body deformation restraining portions 34, 35 may be formed as one body.

Now, the flow of the heating medium in the heat exchanger unit of the artificial lung 1 according to this embodiment will be described referring to FIGS. 3-5. The heating medium flowing into the inside of the artificial lung 1 via the heating medium inflow port 28 passes through the inside of the first header 22 to flow into the inflow side heating medium chamber 41. Then, the heating medium passes through the inflow chamber side opening 33a of the tubular heating medium chamber forming member 32, passes through the medium inflow side passage 37 formed by the abutment portions of the heat exchange body deformation restraining portions 34, 35, and flows between the heat exchange body 31 and the heat exchange body deformation restraining portions 34, 35. In this instance, the heat exchange body 31 is warmed or cooled by the heating medium.

Then, the heating medium passes through the medium outflow side passage 38 formed by the abutment portions of the heat exchange body deformation restraining portions 34, 35, passes through the outflow chamber side opening 33b of the tubular heating medium chamber forming member 32, and flows out into the outflow side heating medium chamber 42 in the tubular heating medium chamber forming member 32. Subsequently, the heating medium passes through the inside of the first header 22 and flows out via the heating medium outflow port 29.

Now, the flow of blood in the artificial lung 1 will be described. In this artificial lung 1, the blood flowing into the artificial lung is distributed via the blood inflow port 24 and flows into the blood guide portion 56 constituting a part of the first blood chamber 11 formed between the tubular core 5 and the tubular heat exchanger unit. The blood flows between the tubular core 5 and the tubular heat exchange body, then passes through the openings 52 located at a position opposed to the first blood guide portion 56, and flows out of the tubular core 5.

The blood flowing out of the tubular core 5 flows into the plurality of grooves 51 on the outside surface of the tubular core 5 located between the inside surface (inner peripheral portion 15) of the hollow fiber membrane bundle 3 and the tubular core 5, and then flows into the gaps in the hollow fiber membrane bundle 3. In the artificial lung 1, the multiplicity of grooves 51 are formed over substantially the whole region of the portion contributing to gas exchange of the hollow fiber membrane bundle 3 (the effective length or the portion not buried in the partition wall), so that the blood can be dispersed to the whole part of the hollow fiber membrane bundle 3, the whole part of the hollow fiber membrane bundle can be utilized, and a relatively high gas exchange performance can be obtained.

Then, the blood makes contact with the hollow fiber membranes where gas exchange is performed, and then the blood flows into the second blood chamber 12 formed between the tubular housing body 21 and the outside surface of the hollow fiber membranes (the outside surface of the hollow fiber membrane bundle 3). The bubbles present in the blood are trapped by the filter member 6, as described above, and eventually enters into the lumens of the hollow fiber membranes 3a.

The blood flowing into the second blood chamber 12 flows out of the artificial lung or is distributed via the blood outflow port 25. In addition, an oxygen-containing gas flowing in via the gas inflow port 26 passes through the inside of the first header 22, flows via the partition wall end face into the hollow fiber membranes, then passes through the inside of the second header 23, and flows out via the gas outflow port 27.

Examples of the materials for forming the members other than the heat exchange body 31, i.e., the materials for forming the tubular housing body 21, the tubular core 5, the first and second headers 22, 23 and the like include polyolefins (e.g., polyethylene, polypropylene), ester resins (e.g., polyethylene terephthalate), styrene-based reins (e.g., polystyrene, MS resin, MBS resin), and polycarbonates.

In addition, the blood contact surfaces in the artificial lung 1 are preferably anti-thrombogenic surfaces. The anti-thrombogenic surfaces can be formed by covering the surfaces with an anti-thrombogenic material and fixing the material. Examples of the antithrombogenic material include heparin, urokinase, HEMA-St-HEMA copolymer, and poly-HEMA.

Figure 6:
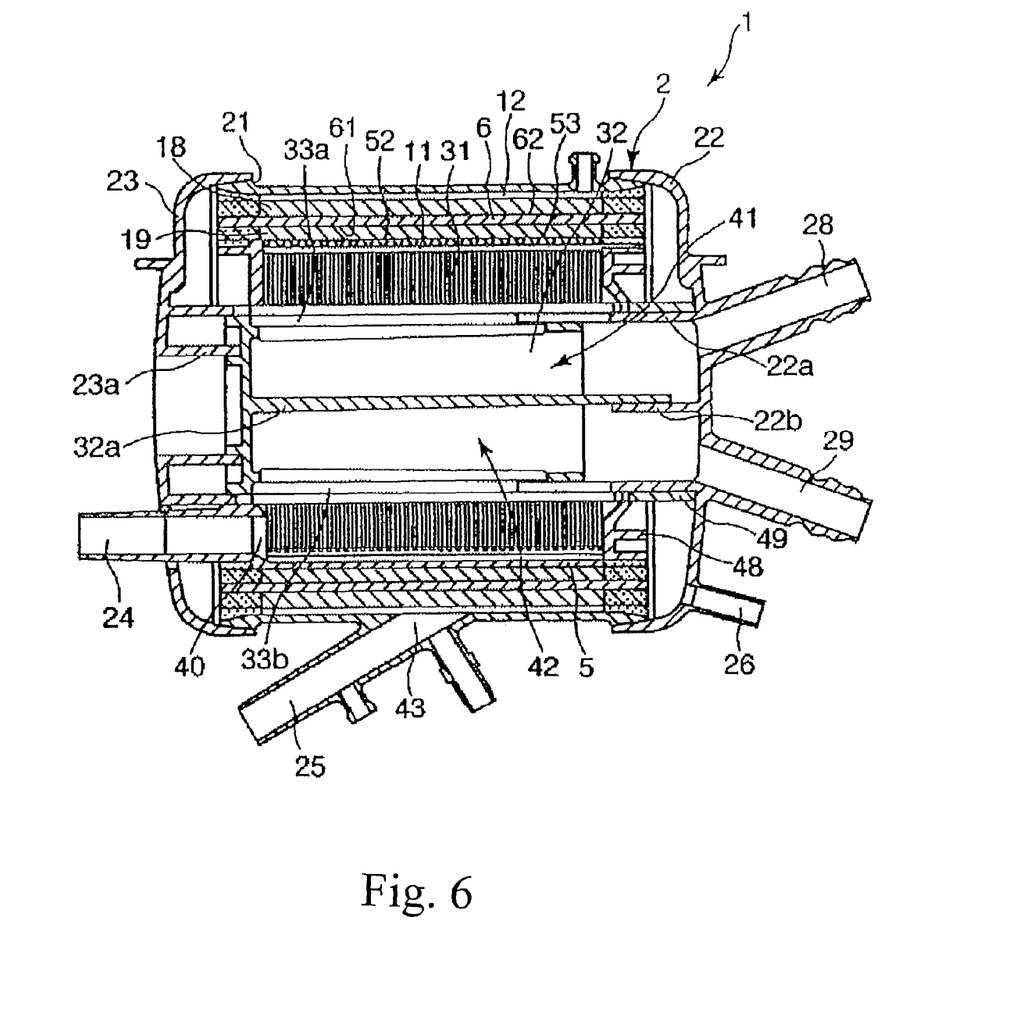
FIG. 6 is a cross-sectional view of an artificial lung according to a second embodiment of the present invention.

FIG. 6 is a cross-sectional view of an artificial lung according to a second embodiment of the present invention. The following description of the second embodiment will focus primarily on the differences between this embodiment and the embodiment described above, with features in the second embodiment that correspond to those in the first embodiment being identified by the same reference numerals. A detailed discussion of features which have already been described will not be repeated in entirety.

This embodiment is the same as the first embodiment, except for the position of the filter member. As shown in FIG. 6, the filter member 6 is provided at an intermediate portion in the thickness (material thickness) direction (the radial direction) of the tubular hollow fiber membrane bundle 3. Specifically, the filter member 6 is provided between an outside layer 18 and an inside layer 19 of the tubular hollow fiber membrane bundle 3.

In addition, an outer peripheral portion 62 and an inner peripheral portion 61 of the filter member 6 are in contact with the outside layer 18 and the inside layer 19, respectively. Namely, the filter member 6 is clamped or situated between the outside layer 18 and the inside layer 19.

The filter member 6 thus arranged makes it possible to relatively reliably trap the bubbles present in the blood flowing from the first blood chamber 11 into the tubular hollow fiber membrane bundle 3 and, hence, to securely prevent the bubbles from flowing out via the blood outflow port.

It is to be understood that the provision of one filter member 6 at an intermediate portion of the tubular hollow fiber membrane bundle 3 is not limitative. For example, a plurality of filter members 6 may be provided.

While the artificial lung according to the present invention has been described above referring to the embodiments shown in the figures, the invention is not limited to these embodiments, and the components of the artificial lung can be replaced by other members having the same or equivalent functions. In addition, components or features other than those described above can be utilized.

What is claimed is:

1. A method of oxygenating blood comprising:
    introducing blood into a blood inflow port communicating with an interior of a housing containing a hollow fiber membrane bundle, the hollow fiber membrane bundle being comprised of a plurality of gas exchanging fiber membranes each having a lumen;
    conveying an oxygen-containing gas through the lumens of the gas exchanging fiber membranes while the blood flows into gaps in the hollow fiber membrane bundle to subject the blood to oxygenation and produce oxygenated blood;
    separating air bubbles in the oxygenated blood from the oxygenated blood by virtue of the oxygenated blood passing through a filter member positioned in contact with the hollow fiber membrane bundle, a pressure differential between a blood side of the gas exchanging fiber membranes and the hollow interior of the gas exchanging fiber membrane lumens causing air bubbles which are trapped by the filter member to enter into the gas exchanging fiber membranes;

conveying the air bubbles separated from the oxygenated blood through the lumens of the gas exchanging fiber membranes;

flowing the blood which has passed through the filter member to a blood chamber in the housing; and conveying the blood in the blood chamber out of the housing by way of a blood outflow port.

2. The method as set forth in claim 1, wherein the blood introduced into the blood inflow port enters an inflow opening portion which opens to an inner peripheral portion side of said hollow fiber membrane bundle, and the blood in the blood chamber enters an outflow opening portion opening to an outer peripheral portion side of the hollow fiber membrane bundle, the blood flowing from the inner peripheral portion side of the hollow fiber membrane bundle to the outer peripheral portion side of the hollow fiber membrane bundle.

3. The method as set forth in claim 1, further comprising subjecting the blood introduced into the blood inflow port to heat exchange treatment in the housing before the blood is oxygenated.

4. The method as set forth in claim 1, wherein the air bubbles separated from the blood by the filter member are conveyed out of the housing other than by way of the blood outflow port.

5. The method as set forth in claim 1, wherein the blood introduced into the housing flows along a plurality of grooves on an outer peripheral surface of a core.

6. The method according to claim 5, wherein the blood entering the housing flows into a blood chamber and then enters the plurality of grooves by way of openings formed in the core.

7. A method of oxygenating blood comprising:
introducing blood into a housing containing a hollow fiber membrane bundle, the hollow fiber membrane bundle being comprised of a plurality of gas exchanging fiber membranes each having a lumen;
subjecting the blood to oxygenation to produce oxygenated blood, the blood being subjected to oxygenation by virtue of the blood introduced into the housing flowing into gaps of the hollow fiber membrane bundle while an oxygen-containing gas passes through the lumens of the fiber membranes;
passing the oxygenated blood through a filter member having a surface in contact with the hollow fiber membrane bundle to separate air bubbles in the oxygenated blood from the oxygenated blood, a pressure differential between a blood side of the fiber membranes and the hollow interior of the fiber membrane lumens causing air bubbles which are trapped by the filter member to enter into the hollow fiber membranes;
conveying the air bubbles separated from the oxygenated blood out of the housing;
conveying the oxygenated blood which has passed through the filter member out of the housing.

8. The method as set forth in claim 7, wherein the blood is introduced into the housing by way of a blood inflow port, the blood entering the blood inflow port entering an inflow opening portion which opens to a first side of the hollow fiber membrane bundle, the blood flowing from the first side of the hollow fiber membrane bundle to a second side of the hollow fiber membrane bundle.

9. The method as set forth in claim 8, further comprising subjecting the blood introduced into the blood inflow port to heat exchange treatment in the housing before the blood is oxygenated.

10. The method as set forth in claim 7, wherein the oxygenated blood which has passed through the filter member is conveyed out of the housing by way of a blood outflow port, and the air bubbles separated from the blood by the filter member are conveyed out of the housing other than by way of the blood outflow port.

11. The method as set forth in claim 7, wherein the filter member through which the oxygenated blood is passed is a mesh filter member.

12. The method as set forth in claim 7, wherein the filter member through which the oxygenated blood is passed is a mesh filter member comprising openings of a size not more than 50 μm.

13. A method of oxygenating blood comprising:
introducing blood into a housing containing a hollow fiber membrane bundle, the hollow fiber membrane bundle possessing a surface and being comprised of a plurality of gas exchanging fiber membranes each having a lumen;
conveying an oxygen-containing gas through the lumens of the gas exchanging fiber membranes;
the blood introduced into the housing being oxygenated as the blood introduced into the housing flows into gaps of the hollow fiber membrane bundle during flow of the oxygen-containing gas through the lumens of the gas exchanging fiber membranes;
separating bubbles from the oxygenated blood by passing the oxygenated blood through a filter member having a surface in contact with the surface of the hollow fiber membrane bundle, a pressure differential between a blood side of the hollow fiber membranes and the hollow interior of the fiber membrane lumens causing air bubbles which are trapped by the filter member to enter into the hollow fiber membranes;
conveying the oxygenated blood which has passed through the filter member out of the housing by way of a blood outflow port; and
conveying the bubbles separated from the oxygenated blood through the lumens of the gas exchanging fiber membranes and removing the bubbles separated from the oxygenated blood out of the housing by way of a gas outlet port different from the blood outflow port.

14. The method as set forth in claim 13, wherein the filter member through which the oxygenated blood is passed is a mesh filter member.

15. The method as set forth in claim 13, wherein the filter member through which the oxygenated blood is passed is a mesh filter member comprising openings of a size not more than 50 μm.

16. The method as set forth in claim 13, wherein the blood is introduced into the housing by way of a blood inflow port and an inflow opening portion which opens to a first side of the hollow fiber membrane bundle.

17. The method as set forth in claim 13, further comprising subjecting the blood introduced into the housing to heat exchange treatment in the housing before the blood is oxygenated.

18. The method as set forth in claim 13, wherein the bubbles separated from the blood by the filter member are conveyed out of the housing through the lumens.

* * * * *